United States Patent
Breunig et al.

(10) Patent No.: US 7,038,001 B2
(45) Date of Patent: *May 2, 2006

(54) METHOD FOR PREPARING SILICONE OILS BY HYDROSILYLATION WITH POLYORGANOHYDROGENOSILOXANES AND UNITS CONTAINING AT LEAST ONE HYDROCARBON RING INCLUDING AN OXYGEN ATOM, IN THE PRESENCE OF A HETEROGENEOUS CATALYTIC COMPOSITION

(75) Inventors: Stefan Breunig, Vienne (FR); Gèrard Mignani, Lyons (FR)

(73) Assignee: Rhodia Chimie, Boulogne-Billancourt Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,244

(22) PCT Filed: Jun. 12, 1997

(86) PCT No.: PCT/FR97/01055

§ 371 (c)(1),
(2), (4) Date: Feb. 19, 1999

(87) PCT Pub. No.: WO97/47677

PCT Pub. Date: Dec. 18, 1997

(65) Prior Publication Data

US 2002/0068807 A1  Jun. 6, 2002

(30) Foreign Application Priority Data

Jun. 12, 1996 (FR) .................................. 96 07272

(51) Int. Cl.
  *C08G 77/08* (2006.01)

(52) U.S. Cl. .............................. 528/15; 528/31; 528/27
(58) Field of Classification Search .................. 528/15, 528/27, 31
See application file for complete search history.

(56) References Cited

U.S. PATENT DOCUMENTS

| | | | | |
|---|---|---|---|---|
| 2,970,150 A | * | 1/1961 | Bailey | 549/215 |
| 3,198,766 A | | 8/1965 | Nitzsche | 260/46.5 |
| 4,064,154 A | * | 12/1977 | Chandra et al. | 528/15 |
| 4,313,988 A | * | 2/1982 | Koshar et al. | 428/40 |
| 4,366,001 A | * | 12/1982 | Ona et al. | 106/287.11 |
| 5,187,251 A | * | 2/1993 | Jachmann et al. | 528/15 |
| 5,232,959 A | * | 8/1993 | Togashi et al. | 523/211 |
| 6,124,418 A | * | 9/2000 | Crivello et al. | 528/15 |
| 6,545,115 B1 | * | 4/2003 | Breunig et al. | 528/31 |

FOREIGN PATENT DOCUMENTS

| | | |
|---|---|---|
| EP | 0 468 305 | 1/1992 |
| EP | 0 533 170 | 3/1993 |
| EP | 0 632 099 | 1/1995 |
| WO | 96 16126 | 5/1996 |

* cited by examiner

*Primary Examiner*—Margaret G. Moore
(74) *Attorney, Agent, or Firm*—Buchanan Ingersoll, P.C.

(57) ABSTRACT

The subject-matter of the invention is a process for the preparation of silicone oils which are weakly colored and low in turbidity by hydrosilylation of polyorganohydrosiloxanes with different or identical synthons comprising at least one hydrocarbon-comprising ring in which is included an oxygen atom, the said reaction being carried out in the presence of a heterogeneous catalytic composition comprising a metal chosen from the group consisting of cobalt, rhodium, ruthenium, platinum and nickel deposited on an inert support.

16 Claims, No Drawings

METHOD FOR PREPARING SILICONE OILS BY HYDROSILYLATION WITH POLYORGANOHYDROGENOSILOXANES AND UNITS CONTAINING AT LEAST ONE HYDROCARBON RING INCLUDING AN OXYGEN ATOM, IN THE PRESENCE OF A HETEROGENEOUS CATALYTIC COMPOSITION

The present invention relates to a novel process for the preparation of functionalized silicone oils comprising at least one hydrocarbon-comprising ring in which is included an oxygen atom. In particular, a subject-matter of the present invention is a process for hydrosilylation between polyorganohydrosiloxanes and unsaturated units comprising at least one hydrocarbon-comprising ring in which is included an oxygen atom.

Reactions between polyorganohydrosiloxanes and olefins or acetylenic hydrocarbons are very well-known. The polyorganohydrosiloxanes are, for example, of formulae:

—Me$_3$SiO—(MeHSiO)$_n$—(Me$_2$SiO)$_m$—SiMe$_3$, in which n and m are integers or fractions such that $1 \leq n \leq 1000$ and $0 < m \leq 1000$;

—Me$_2$HSiO—(MeHSiO)$_o$—(Me$_2$SiO)$_p$—SiHMe$_2$, in which o and p are integers or fractions such that $0 < o \leq 1000$ and $0 < p \leq 1000$.

Numerous synthons can functionalize polyorganohydrosiloxanes; for example, alkenes, styrenes, allyl alcohols, allyloxy ethers or allylamines are used as synthons.

These reactions are very commonly used for the synthesis of functionalized silicone oils and the oils obtained have applications in highly varied fields, such as antiadhesion or lubrication.

Functionalized oils can in particular be prepared with 1,2-epoxy-4-vinylcyclohexane synthons. By way of application, these functionalized silicone oils are subsequently thermally crosslinked in the presence of an acidic catalyst, such as hydrochloric acid or sulphuric acid, or photochemically crosslinked in the presence, for example, of a cationic photoinitiator, for the preparation of antiadhesive films for paper and/or plastics.

A very large number of catalytic compositions are used in hydrosilylation reactions. The most well-known catalytic compositions comprise metals, such as platinum, rhodium, cobalt or palladium. Specific examples of such catalytic compositions are platinum halides and rhodium halides, for example H$_2$PtCl$_6$, PtCl$_2$, (RhCl3·xH$_2$O), complexes of platinum with siloxanes having unsaturated groups, complexes of platinum with olefins and cationic complexes of platinum with nitrites as ligands.

The catalytic compositions used in the hydrosilylation reaction are generally homogeneous catalytic compositions, i.e. the said compositions are dissolved in the reaction mixture. One of the most widely employed is the Karstedt catalytic composition disclosed in particular in U.S. Pat. No. 3,775,452; this Karstedt composition is composed of platinum complexes, the platinum having a formal and true degree of oxidation of zero (0), with the formula:

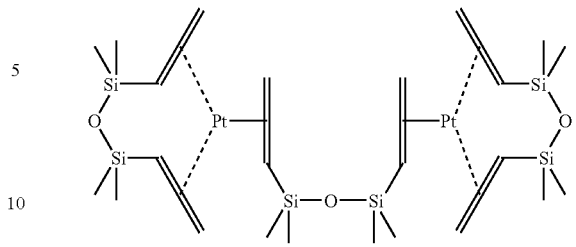

However, during the hydrosilylation reaction according to the processes of the prior art, isomerization reactions are observed, to varying degrees, within the unsaturated synthons, which requires operating with a molar excess of synthon with respect to the polyorganohydrosiloxane in the reaction mixture. This proportionate excess of synthon leads to an additional cost in the industrial implementation of the process. It would thus be desirable to reduce the necessary proportion of synthon, which would be reflected by a not insignificant saving with regard to the process.

In addition, the hydrosilylation processes of the prior art are not or not very suited to hydrosilylation reactions between polyorganohydrosiloxanes and synthons comprising a ring in which is included an oxygen atom (epoxide, and the like). The latter, during the devolatilization stage, has a tendency to open and to cause uncontrolled polymerization and crosslinking reactions (formation of gum and/or of resin) of the functionalized oils which are initiated by the presence of traces of the usual catalytic compositions, such as homogeneous catalytic compositions, which also catalyze the polymerization of rings including an oxygen atom.

Furthermore, the functionalized silicone oils obtained from processes using homogeneous catalysis are generally coloured, of the order of 120 to 300 hazen units, which for this reason limits their fields of use which can be envisaged, in particular in the field of transparent antiadhesive films for paper or for transparent films (for example of polyester type). This colouring is generally due to the presence, in the functionalized oils, of metal aggregates or of colloids with a nanometric size derived from the homogeneous catalytic compositions used in the hydrosilylation processes of the prior art. In these cases, the functionalized silicone oils require additional filtration and purification stages in order to be able to be useable after crosslinking in the field of transparent films; these additional stages make the industrial implementation expensive and thus of little viability economically.

The Applicant Company has developed a novel process for the preparation of functionalized silicone oils by hydrosilylation which makes it possible to significantly reduce isomerization reactions within the unsaturated synthon and, furthermore, to very substantially reduce, during the devolatilization stage, the opening of a ring including an oxygen atom present on the unsaturated synthon.

The process employed makes it possible to obtain transparent and translucent functionalized silicone oils, which makes it possible to use the silicone oils according to the invention in applications which require this property, without requiring additional filtration or purification stages.

In particular, the silicone oils obtained from the process of the invention can be used after crosslinking in the field of inks, in the field of varnishes and in the field of coatings, in particular films, which are transparent and/or antiadhesive, by applications to supports of highly varied natures; for example, papers, glasses, plastics and/or metals.

In addition, the oils prepared are stable on storage.

Furthermore, the oils obtained according to the invention are devoid of toxicity; this is because, due to employing a heterogeneous catalytic composition, virtually no metals are found in the said oils.

According to the hydrosilylation process of the present invention, the polyorganohydrosiloxane is reacted with different or identical synthons comprising a hydrocarbon-comprising ring in which is included at least one oxygen atom. This reaction is carried out in the presence of a heterogeneous catalytic composition comprising a metal chosen from the group consisting of cobalt, rhodium, ruthenium, platinum, palladium and nickel deposited on an inert support. The metal of the catalytic composition is preferably platinum.

The amount of metal present in the heterogeneous catalytic composition is between 0.005% and 5% with respect to the weight of the inert support. This amount of metal is also between 1 and 1000 ppm with respect to the weight of the polyorganohydrosiloxane.

By definition, heterogeneous catalytic composition is understood to mean a catalytic composition, which can be solid or liquid, which is not dissolved in the reaction mixture, i.e. the reaction mixture comprises at least two phases, one of which is formed by the catalytic composition.

The metal is deposited on varied inert supports, such as carbon black, charcoal, alumina, treated or untreated silica, barium sulphate or crosslinked silicones. The particle size of the catalytic supports is advantageously greater than 10 μm, in order to be able to be filtered well without requiring filtration adjuvants. Thus, this particle size is such that it is possible to greatly reduce the filtration time.

The synthons comprise at least one hydrocarbon-comprising ring in which is included an oxygen atom and have the formula:

(1)

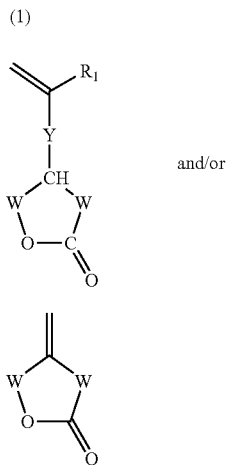

and/or in which:
the symbols W are identical or different and correspond to a divalent hydrocarbon-comprising radical chosen from linear or branched alkylene radicals having from 1 to 12 carbon atoms, it being possible for one of the symbols W to be a free valency;
the symbol Y corresponds to a free valency or a divalent radical chosen from linear or branched alkylene radicals having from 1 to 12 carbon atoms which can comprise a heteroatom, preferably an oxygen atom;
the symbol $R_1$ corresponds to a hydrogen atom or monovalent hydrocarbon-comprising radical chosen from linear or branched alkyl radicals having from 1 to 12 carbon atoms and preferably a hydrogen atom or a methyl radical;

(2)

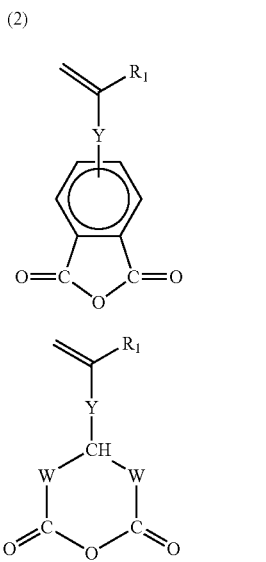

in which:
the symbols W are identical or different and correspond to a divalent hydrocarbon-comprising radical chosen from linear or branched alkylene radicals having from 1 to 12 carbon atoms, it being possible for one of the symbols W to be a free valency;
the symbol Y corresponds to a free valency or a divalent radical chosen from linear or branched alkylene radicals having from 1 to 12 carbon atoms which can comprise a heteroatom, preferably an oxygen atom;
the symbol $R_1$ corresponds to a hydrogen atom or monovalent hydrocarbon-comprising radical chosen from linear or branched alkyl radicals having from 1 to 12 carbon atoms and preferably a hydrogen atom or a methyl radical;

(3)

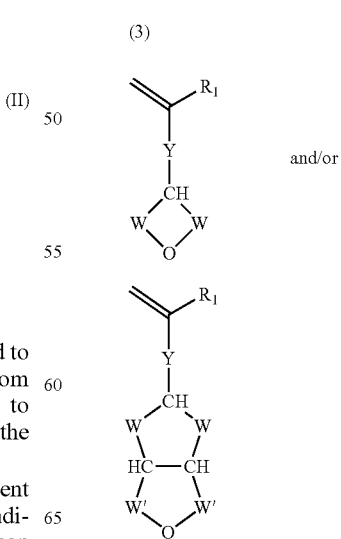

in which:

the symbols W are identical or different and correspond to a divalent hydrocarbon-comprising radical chosen from linear or branched alkylene radicals having from 1 to 12 carbon atoms which can comprise at least one hydroxyl functional group, it being possible for one of the symbols W to be a free valency for (V) and it being possible for both symbols W simultaneously to be a free valency for (VI);

the symbols W' are identical or different and correspond to a divalent hydrocarbon-comprising radical chosen from linear or branched alkylene radicals having from 1 to 12 carbon atoms, it being possible for at least one of the symbols W' to be a free valency;

the symbol Y corresponds to a free valency or a divalent radical chosen from linear or branched alkylene radicals having from 1 to 12 carbon atoms which can comprise a heteroatom, preferably an oxygen atom;

the symbol $R_1$ corresponds to a hydrogen atom or monovalent hydrocarbon-comprising radical chosen from linear or branched alkyl radicals having from 1 to 12 carbon atoms and preferably a hydrogen atom or a methyl radical; and (4)

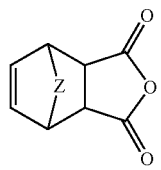
(VII)

in which;

the symbols W are identical or different and correspond to a free valency or a divalent hydrocarbon-comprising radical chosen from linear or branched alkylene radicals having from 1 to 2 carbon atoms;

the symbol Z corresponds to a divalent radical chosen from a carbon atom or a heteroatom.

The hydrocarbon-comprising ring in which is included the oxygen atom preferably comprises at most 8 atoms in the said ring. Furthermore, the best results in agreement with the hydrosilylation process of the invention are obtained with synthons which only comprise one hydrocarbon-comprising ring in which is included an oxygen atom. In particular, the synthons used which give good results (see examples below) have the formula:

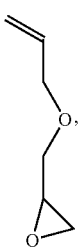
(VIII)

-continued

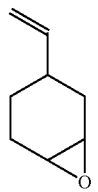
(IX)

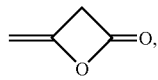
(X)

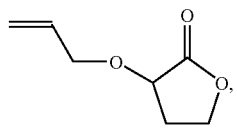
(XI)

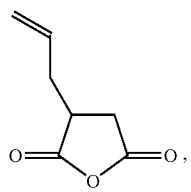
(XII)

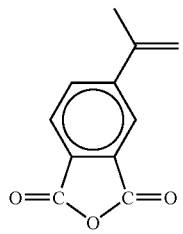
(XIII)

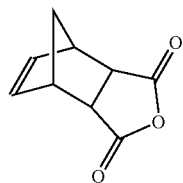
(XIV)

and

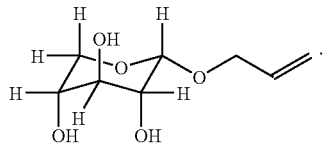
(XV)

The synthons which react with the polyorganohydrosiloxane are generally identical synthons. The polyorganohydrosiloxane/synthons molar ratio is between 0.01 and 100, preferably between 0.1 and 10.

The polyorganohydrosiloxanes used in the processes according to the invention are very diverse in nature. These polyorganohydrosiloxanes can be linear or cyclic and have the mean formulae:

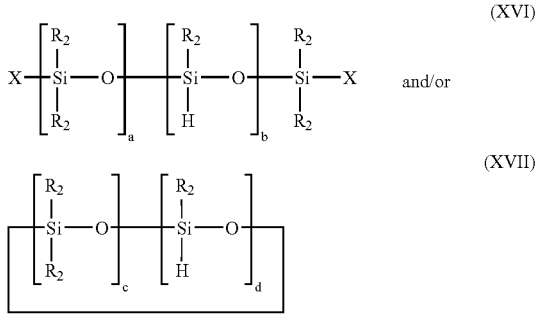

(XVI) and/or (XVII)

in which:
the symbols $R_2$ are identical or different and correspond to a monovalent hydrocarbon-comprising radical chosen from the phenyl radical and linear or branched alkyl radicals having from 1 to 6 carbon atoms, preferably 1 to 3 carbon atoms;
the symbols X are identical or different and correspond to a monovalent radical chosen from $R_2$, a hydrogen atom, a methoxy radical and an ethoxy radical;
a and b are integers or fractions, such that:
  $0 < a \leqq 200$, preferably $0 < a \leqq 99$,
  $0 \leqq b \leqq 200$, preferably $1 < b \leqq 100$, and at least one of the two X groups corresponds to the hydrogen radical if b=0,
  $5 < a+b \leqq 200$, preferably $10 < a+b \leqq 100$;
c and d are integers or fractions, such that
  $0 < c < 5$, preferably $0 < c < 3$,
  $1 < d < 10$, preferably $1 < d < 5$,
  $3 < a+b < 10$, preferably $3 < a+b < 5$.

In the context of the invention, various types of heterogeneous catalytic compositions can be used.

Use may be made, as non-limiting examples, of platinum on charcoal or carbon black, such as the catalytic composition comprising 2.5% by weight of platinum deposited on the CECA 2S support developed by the company Ceca, the SCAT 20 catalytic composition (1% Pt) from the company Engelhard or the 88 231 catalytic composition (1% Pt) from the company Heraeus. In this case, the platinum can be deposited on this type of support by deposition of chloroplatinic acid, followed by a neutralization and by a reduction. Likewise, the use of platinum on alumina, preferably of α type, such as the CAL 101 catalytic composition (0.3% Pt, SCS9 support composed of α-alumina) sold by the company Procatalyse or the 88 823 catalytic composition from the company Heraeus (0.5% Pt on α-alumina), gives good results.

The process according to the invention can be carried out according to various alternative forms. In particular, it is possible to use a first implementation in which the combined reactants and catalytic composition are mixed in the reaction mixture (batch type). The second implementation of the process according to the invention can be continuous with a stationary bed of heterogeneous catalytic composition over which pass the polyorganohydrosiloxane to be functionalized and the synthon. This type of implementation is advantageous in the case where the size of the grains of the inert support of the catalytic composition is greater than 100 pm.

In the context of its experimental tests, the Applicant Company has developed an advantageous process in agreement with the first implementation. This process for hydrosilylation between a polyorganohydrosiloxane and an unsaturated synthon comprises the following stages:

(a) an amount of 5 to 5000 ppm, preferably of 10 to 100 ppm, of heterogeneous catalytic composition with respect to the total mass of the reactants is introduced under an inert gas into the reaction mixture;

(b) the synthon is introduced into the reaction mixture;

(c) the said mixture is heated to a temperature of between 25° C. and 200° C. and preferably between 50° C. and 160° C.;

(d) the polyorganohydrosiloxane is subsequently introduced over a period of time of between 0 and 24 hours, preferably between 2.5 and 5 hours, the synthon/silicone molar ratio being between 1 and 1.10;

(e) the reaction mass is subsequently filtered in order to separate the heterogeneous catalytic composition and the functionalized silicone oil; and (f) the functionalized silicone oil is finally devolatilized.

This advantageous process can be carried out in bulk, which means that the reaction between the polyorganohydrosiloxane and the synthon is carried out in the absence of solvent. However, numerous solvents, such as toluene, xylene, octamethyltetrasiloxane, cyclohexane or hexane, can be used.

Furthermore, the molar amount of synthon poured in during the stage (b) is less than that which is used for a conventional process of the prior art. The synthon/polyorganohydrosiloxane molar ratio is advantageously between 1 and 1.05, without harming the quality of the functionalized oils obtained and the reaction yield.

The filtration stage (e) makes it possible, if appropriate, to remove any remaining trace of turbidity from the functionalized silicone oil obtained. Furthermore, the heterogeneous catalytic composition can be recovered and then again reused, without requiring regeneration, with or without washing, and without a substantial fall in activity with regard to its performance being recorded.

The functionalized silicone oils obtained in agreement with the invention and in particular according to the advantageous process developed are very stable and do not undergo changes during the devolatilization stage. Their viscosities are very substantially lower with respect to those of the oils obtained from the same reactants and according to the processes of the prior art, in particular those using homogeneous catalysts.

For example, the viscosity of the oils of formula (XVIII) functionalized with 1,2-epoxy-4-vinylcyclohexane, obtained in agreement with our process, is of the order of 200 to 290 mpa·s, which reflects the absence of opening of the rings comprising an oxygen atom and thus the absence of polymerization reactions, including during the devolatilization, due to the opening of these rings.

In addition, the viscosity of the oils obtained is stable on storage over a very long period of time, which means that no side reaction takes place in the said oils (no formation of gum and/or of resin over time).

Furthermore, the oils prepared in agreement with the processes according to the invention are virtually transparent, with zero colouring and zero turbidity. This absence of colouring is apparent in particular with the catalytic compositions with an inert support composed of carbon black. In the context of our invention, zero colouring is understood to mean a colouring of less than 90 hazen units and preferably of less than 40 hazen units. A colouring of between 40 and 90 hazen units is observed solely in the case where the synthons are themselves coloured at the beginning before the hydrosilylation; the colouring is in no case due to the implementation of the process of the invention. If the synthons are colourless before reaction, the oils prepared have a colouring of less than 40 hazen units. As regards the turbidity, the oils are nonturbid when their turbidity is less than 1 NTU and/or only exhibit minimum traces of turbidity.

These oils also have a very low content of metal resulting from the catalytic composition, which very much limits the undesirable reactions which the metal could cause if its content were higher. For example, in the case of oils obtained according to the invention in the presence of a catalytic composition comprising in particular platinum, it is possible to mix the said oils with other molecules comprising ≡SiH functional groups and molecules comprising unsaturated bonds without the risk of a further hydrosilylation reaction between these molecules.

The level of epoxy quantitatively determined in the oils obtained according to the invention is very high and the level of epoxy quantitatively determined/theoretical epoxy level ratio is between 0.95 and 1, this theoretical epoxy level corresponding to the level of ≡SiH quantitatively determined on the polyorganohydrosiloxane before reaction.

The silicone oils according to the invention, because of their properties, are thus employed as additive (for example, as diluent) or as main component (for example, as resin) in the preparation of crosslinkable compositions employed to prepare inks, varnishes and/or coatings which are transparent and colourless, These crosslinkable compositions generally comprise a photoinitiator and an organic and/or silicone resin with epoxy and/or acrylate functionality; in addition, these compositions can comprise a diluent and/or a solvent. These compositions can be crosslinked as the case may be, for example under U.V. radiation and/or under an electron beam.

EXAMPLES

The examples below illustrate the preparation of functionalized silicone oils obtained according to the process of the present invention.

Examples 1 to 9 relate to the synthesis of silicone oils functionalized by 1,2-epoxy-4-vinylcyclohexane synthons with a polyorganohydrosiloxane for which the number of milliequivalents of ≡SiH functional group is 128 per 100 g of polyorganohydrosiloxane and which has the mean formula (XVIII):

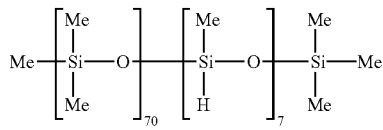

Examples 11 to 14 relate to the synthesis of silicone oils functionalized by 1,2-epoxy-4-vinylcyclohexane synthons with a polyorganohydrosiloxane of mean formula (XVI) for which the values of X, a and b are specified in each example.

Examples 1 to 3 relate to preparations according to the prior art and Examples 4 to 14 relate to preparations in agreement with the subject-matter of our invention.

The reaction scheme is as follows:

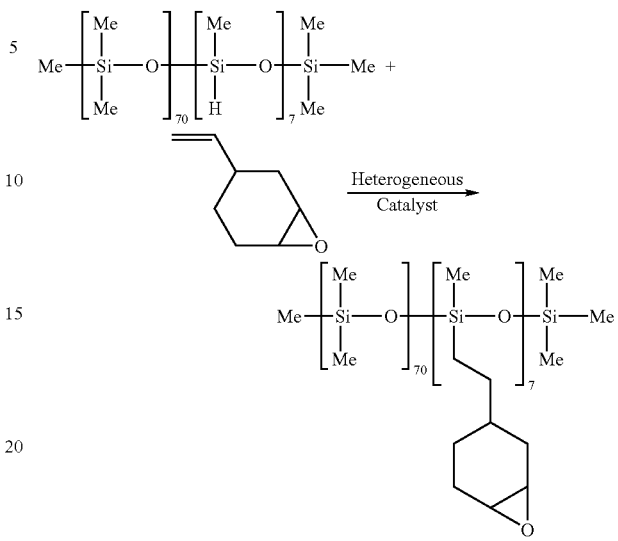

Quantitative determination of the ≡SiH groups present on the functionalized oils obtained is carried out by gas analysis. The amount of $H_2$ given off during the reaction between the functionalized silicone oil obtained and 1-butanol in the presence of potassium hydroxide as catalyst (2 g of KOH in 50 ml of 1-butanol) is measured.

The colouring of the functionalized oils obtained is measured with the help of an LTh1 liquid tester device from Dr. Lange using two beams for the measurement by transmission.

The turbidity of the functionalized oils obtained is measured with the help of a Haack turbidimeter by light dispersion (measurement by ratio).

The platinum content in the functionalized oils obtained is measured by ICP-MS.

The viscosity of the functionalized oils obtained is measured with the help of a Brookfield device according to the dynamic method (by shearing).

The quantitative determination of the epoxy groups on the functionalized oils obtained is measured with the help of a potentiometric device of 716 DMS Titrino type from Metrohm according to the method of I. M. Kolthoff and P. J. Elving (Treatise on Analytical Chemistry, Part II, Vol. 14, p. 288).

Example 1

6.07 μl of Karstedt homogeneous catalytic composition comprising 11.6% Pt (11.6 ppm of Pt in the mixture) and 8.68 g (69.89 mmol, 5% excess) of 1,2-epoxy-4-vinylcyclohexane were introduced under argon into a 100 ml three-necked flask equipped with a vertical stirrer, a reflux condenser, a thermometer and a septum.

This mixture is heated to 90° C. 52 g (66.56 mmol) of polyorganohydrosiloxane of formula (XVIII) are then run in over a period of 1 hour.

After the reactant has been run in, the degree of conversion of SiH is 99.7%.

After devolatilization at 90° C. for 2 hours, a functionalized oil is recovered which has a viscosity of 930 mPa·s.

The colouring of the oil is 240 hazen units and the platinum content is 11.6 ppm.

The level of epoxy quantitatively determined/theoretical epoxy level ratio is 0.91.

Example 2

6.07 µl of Karstedt homogeneous catalytic composition comprising 11.6% Pt (11.6 ppm of Pt in the mixture) and 8.68 g (69.89 mmol, 5% excess) of 1,2-epoxy-4-vinylcyclohexane were introduced under argon into a 100 ml three-necked flask equipped with a vertical stirrer, a reflux condenser, a thermometer and a septum.

The mixture is heated to 90° C. 52 g (66.56 mmol) of polyorganohydrosiloxane of formula (XVIII) are then run in over a period of 1 hour.

After the reactant has been run in, the degree of conversion of SiH is 99.7%.

Heating is continued for 3 hours. After filtration, the oil is devolatilized at 120° C. for 2 hours.

The functionalized oil obtained is crosslinked and exists in solid form.

Example 3

175 mg of milled heterogeneous catalyst comprising 1% Pt on a support composed of $TiO_2$, 16.7 g of toluene and 2.5 g (20.2 mmol) of 1,2-epoxy-4-vinylcyclohexane were introduced under argon into a 100 ml three-necked flask equipped with a vertical stirrer, a reflux condenser, a thermometer and a septum.

The mixture is heated to 90° C. 15 g of polyorganohydrosiloxane of formula (XVIII) are then run in over a period of 3 hours.

After the reactant has been run in, the degree of conversion is 91.7%. 2 hours later, the degree is 96.6% and then reaches 97.4% 20 hours after the reactant has been run in.

The reaction mixture is filtered on a Eurofiltec R3506 filter under a pressure of $3.5 \times 10^5$ Pa.

The oil obtained is then devolatilized using a rotary evaporator at 100° C. under a vacuum of $2 \times 10^2$ Pa.

A functionalized oil is recovered which is highly coloured, of the order of 2430 hazen units, which has a platinum content of 8.1 ppm and which has a viscosity of 1460 mPa·s. The level of epoxy quantitatively determined/calculated epoxy level ratio is 0.91.

Example 4

3.89 g of non-milled heterogeneous catalytic composition of CAL 101 type (100 ppm of Pt in the mixture) and 16.7 g (0.134 mol, 5% excess) of 1,2-epoxy-4-vinylcyclohexane were introduced under argon into a 250 ml three-necked flask equipped with a vertical stirrer, a reflux condenser, a thermometer and a septum.

The mixture is heated to 90° C. 100 g (0.128 mol) of polyorganohydrosiloxane of formula (XVIII) are then run in over a period of 3 hours.

After the reactant has been run in, the degree of conversion of SiH is 98.6%. 2 hours after the reactant has been run in, the degree of conversion is 100%.

The reaction mass is filtered through sintered glass with a clarcel precoat. Devolatilization is carried out using a rotary evaporator at 100° C. under a vacuum of $2 \times 10^2$ Pa for 2 hours.

A perfectly transparent functionalized oil is recovered (colouring of the order of 83 hazen units and no turbidity). The viscosity measured is 290 mPa·s and the platinum content is 2.1 ppm. After storing for 3 months (at room temperature and under nitrogen), the viscosity is found to be identical.

The level of epoxy quantitatively determined/calculated epoxy level ratio is 0.96.

Example 5

4.668 g of heterogeneous catalytic composition comprising 2.5% Pt on a CECA 2S support (100 ppm of Pt) and 166.9 9 (1.344 mol, 5% excess) of 1,2-epoxy-4-vinylcyclohexane were introduced under argon into a 2 liter three-necked flask equipped with a vertical stirrer, a reflux condenser, a thermometer and a septum.

The mixture is heated to 90° C. 1 kg (1.28 mol) of polyorganohydrosiloxane of formula (XVIII) is run in over a period of 3 hours.

After the reactant has been run in, the degree of conversion of SiH is 96.4% and this reaches 97.5% after 2 hours and then 99.7% after 5 hours.

After filtration, devolatilization is carried out using a rotary evaporator at 100° C. under a vacuum of $2 \times 10^2$ Pa.

A functionalized oil is recovered which has a viscosity of 300 mPa·s. After storing for 3 months (at room temperature and under nitrogen), the viscosity is found to be identical.

The colouring is 45 hazen units and the platinum content is less than 0.16 ppm. The level of epoxy quantitatively determined/calculated epoxy level ratio is 0.96. No turbidity observed.

Example 6

All the washed, dried and recovered heterogeneous catalytic composition from Example 5 and 16.7 g (0.1344 mol, 5% excess) of 1,2-epoxy-4-vinylcyclohexane were introduced under argon into a 250 ml three-necked flask equipped with a vertical stirrer, a reflux condenser, a thermometer and a septum.

The mixture is heated to 90° C. 100 g (0.128 mol) of polyorganohydrosiloxane of formula (XVIII) are run in over a period of 3 hours.

After the reactant has been run in, the degree of conversion of SiH is 87.0%. 2 hours after the reactant has been run in, the degree reaches 94.6%, then 95% 8 hours after and 96.2% 24 hours after.

The reaction mass is filtered through sintered glass with a clarcel precoat, Devolatilization is carried out using a rotary evaporator at 100° C. under a vacuum of $2 \times 10^2$ Pa for 2 hours.

A functionalized oil is recovered which has a viscosity of 270 mPa·s. After storing for 3 months (at room temperature and under nitrogen), the viscosity is found to be identical.

The colouring is 35 hazen units and the platinum content is less than 0.15 ppm.

The level of epoxy quantitatively determined/calculated epoxy level ratio is 0.92.

Turbidity is not observed.

Example 7

0.360 g of heterogeneous catalytic composition comprising 2.5% Pt on a CECA 2S support and 13.9 g (0.112 mol, 5% excess) of 1,2-epoxy-4-vinylcyclohexane were introduced under argon into a 100 ml three-necked flask equipped with a vertical stirrer, a reflux condenser, a thermometer and a septum. The mixture is heated to 90° C. 90 g (0.107 eq.) of polyorganohydrosiloxane of formula (XVIII) are run in over a period of 3 hours.

After the reactant has been run in, the degree of conversion of SiH is 90.3% and this reaches 99.1% 8 hours later.

After filtration, devolatilization is carried out at 120° C. under a vacuum of $2\times10^2$ pa for 2 hours.

A functionalized oil is recovered which has a viscosity of 320 mPa·s. After storing for 3 months (at room temperature and under nitrogen), the viscosity is found to be identical.

The colouring is 25 hazen units and the platinum content is less than 0.17 ppm.

The level of epoxy quantitatively deteriftined/calculated epoxy level ratio is 0.96.

No turbidity observed.

Example 8

0.233 g of heterogeneous catalytic composition (5% Pt on a support composed of barium sulphate) from the company Heraeus (100 ppm of Pt in the mixture) and 16.7 g (0.1344 mol, 5% excess) of 1,2-epoxy-4-vinylcyclohexane were introduced under argon into a 250 ml three-necked flask equipped with a vertical stirrer, a reflux condenser, a thermometer and a septum.

The mixture is heated to 90° C. 100 g (0.128 mol) of polyorganohydrosiloxane of formula (XVIII) are then run in over a period of 3 hours.

After the reactant has been run in, the degree of conversion of SiH is 63.3%. 2 hours after the reactant has been run in, this degree reaches 91.4% and 93.8% 5 hours after the reactant has been run in. 24 hours after, the degree of conversion is 93.1%.

Devolatilization is carried out using a rotary evaporator at 100° C. under a pressure of $2\times10^2$ Pa for 2 hours.

A functionalized oil is recovered which has a viscosity of 280 mPa·s. After storing for 3 months (at room temperature and under nitrogen), the viscosity is found to be identical.

The colouring is 57 hazen units and the platinum content is less than 4–5 ppm.

The level of epoxy quantitatively determined/calculated epoxy level ratio is 0.96.

No turbidity observed.

Example 9

7.78 g of unmilled heterogeneous catalytic composition of CAL 101 type (100 ppm of Pt in the mixture) are introduced into a U-shaped tube equipped with a thermometer and flushing is carried out with argon.

33.4 g of 1,2-epoxy-4-vinylcyclohexane (0.2688 mol, 5% excess) are introduced into a 500 ml three-necked flask connected to the U-shaped tube. The 1,2-epoxy-4-vinylcyclohexane passes into the U-shaped tube containing the catalytic composition (peristaltic pump with rate=100 ml/min) and then returns to the round-bottomed flask.

The reaction mixture is heated to 90° C. 200 g of polyorganohydrosiloxane of formula (XVIII) are then run into the three-necked flask over a period of 3 hours. The polyorganohydrosiloxane and 1,2-epoxy-4-vinylcyclohexane mixture is subsequently passed over the catalytic composition.

After the reactant has been run in, the degree of conversion of the SiH units is 94.8% and, 2 hours after this, the degree reaches 98.4% to ultimately reach 100%.

The reaction mixture is filtered through sintered glass with a clarcel precoat. Devolatilization is carried out using a rotary evaporator at 100° C. under a vacuum of $2\times10^2$ Pa for 2 hours.

A functionalized oil is recovered which has a viscosity of 280 mPa·s. After storing for 3 months (at room temperature and under nitrogen), the viscosity is found to be identical.

The colouring is 114 hazen units and the platinum content is 2.9 ppm.

The level of epoxy quantitatively determined/calculated epoxy level ratio is 0.97.

No turbidity observed.

The catalytic composition is recovered and washed with toluene as soon as the reaction is complete (8 h after the reactant has begun to be run in) and then it is dried with a stream of argon.

Example 10

All the washed and dried heterogeneous catalytic composition of CAL 101 type recovered from Example 9 is introduced into a U-shaped tube equipped with a thermometer and then the assembly is conditioned under argon.

33.4 g of 1,2-epoxy-4-vinylcyclohexane (0.2688 mol, 5% excess) are charged to a 500 ml three-necked flask. The 1,2-epoxy-4-vinylcyclohexane is passed over the catalytic composition contained in the U-shaped tube and then returns to the round-bottomed flask (under the action of a peristaltic pump with rate=100 ml/mn).

The reaction mixture is heated to 90° C. 200 g of polyorganohydrosiloxane of formula (XVIII) are subsequently run in over a period of 3 hours. The mixture of polyorganohydrosiloxane of formula (XVIII) and of 1,2-epoxy-4-vinylcyclohexane is subsequently passed over the catalytic composition (under the action of a pump).

After the reactant has been run in, the degree of conversion of the SiH units is 92.4%. 2 hours after this operation of running in the reactant has finished, the degree of conversion is 94.1% and then, 8 hours after, this level reaches 95.4%.

The reaction mass is filtered through sintered glass with a clarcel precoat. Devolatilization is carried out using a rotary evaporator at 100° C. under a pressure of $2\times10^2$ Pa for 2 hours.

A functionalized oil is recovered which has a viscosity of 270 mPa·s. After storing for 3 months (at room temperature and under nitrogen), the viscosity is found to be identical.

The modified silicone oil obtained is transparent; its colouring is 83 hazen units and the platinum content is 2.1 ppm.

The level of epoxy quantitatively determined/calculated epoxy level ratio is 0.92.

No turbidity observed.

Example 11

2.045 g of heterogeneous catalytic composition comprising 3% Pt on a dried black charcoal support, with the commercial reference 7075 from Engelhard, and 13.46 g (0.108 mol, 5% excess) of 1,2-epoxy-4-vinylcyclohexane were introduced under argon into a two liter four-necked flask equipped with a vertical stirrer, a reflux condenser, a thermometer and a septum cap.

The mixture is heated to 100° C., 600 g (0.103 eq.) of polyorganohydrosiloxane of formula (XVI), in which $X=CH_3$, a=225 and b=2, are run in over a period of 2 hours.

After the reactant has been run in, the degree of conversion of SiH is 64.5%. After 23 hours, it is 83.3%. After heating to 120° C., the degree of conversion of SiH is 100% after 5 days.

After filtration, devolatilization is carried out at 120° C. under a vacuum of 1×10² Pa for 5 hours.

A functionalized oil is recovered which has a viscosity of 610 mPa·s. This viscosity is found to be unchanged after storing for three months at room temperature under nitrogen.

The colouring is 30 hazen units and the platinum content is less than 0.11 ppm.

Turbidity is not observed.

Example 12

2.55 g of heterogeneous catalytic composition comprising 2.5% Pt on a CECA 2S support comprising 52% by mass of water and 2049 g (16.5 mol, 10% excess) of 1,2-epoxy-4-vinylcyclohexane were introduced under argon into a 3.5 liter reactor equipped with a vertical stirrer, a reflux condenser, a dip pipe, a thermometer and a septum cap.

The mixture is heated to 110° C. 1007 g (15 eq.) of polyorganohydrosiloxane of formula (XVI), in which X=H, a=1 and b=0, are run in over a period of five hours via the dip pipe.

After the reactant has been run in, the degree of conversion of SiH is 99.98%.

After filtration, devolatilization is carried out at 120° C. under a vacuum of less than 1×10² Pa for 10 h.

A functionalized oil is recovered which has a viscosity of 51.3 mPa·s. This viscosity is unchanged after storing for three months at room temperature under nitrogen.

The colouring is 30 hazen units and the platinum content is less than 0.11 ppm.

Turbidity is not observed (0.2 NTU).

Example 13

3.74 g of heterogeneous catalytic composition comprising 2.5% Pt on a dried CECA 2S support and 433.85 g (3.8 mol, 5% excess) of allyl glycidyl ether were introduced under argon into a two liter four-necked flask equipped with a vertical stirrer, a reflux condenser, a thermometer and a septum cap.

The mixture is heated to 130° C. 500 g (3.62 eq.) of polyorganohydrosiloxane of formula (XVI), in which X=R, a=9 and b=4.5, are run in over a period of 5 hours.

After the reactant has been run in, the degree of conversion of SiH is 92.7%. After 10 hours, it is 99.8%.

After filtration, devolatilization is carried out at 120° C. under a vacuum of 1×10² Pa for 5 hours.

A functionalized oil is recovered which has a viscosity of 62 mPa·s. This viscosity is unchanged after storing for three months at room temperature under nitrogen.

The colouring is 25 hazen units and the platinum content is less than 0.18 ppm. turbidity is not observed.

Example 14

3.06 g of heterogeneous catalytic composition comprising 3% Pt on a dried black charcoal support, of reference 7075 from the company Engelhard, 20 g of p-xylene and 6.74 g (41 mmol, 10% excess) of nadic anhydride were introduced under argon into a 100 ml four-necked flask equipped with a vertical stirrer, a reflux condenser, a thermometer and a septum cap.

The mixture is heated to 120° C. 10 g (37.3 meq.) of polyorganohydrosiloxane of formula (XVI), in which X=CH₃, a=9.1 and b=4, are run in over a period of two hours.

After 24 hours, the degree of conversion is 41.7% and then 92.4% after 72 hours, 98.9% after 96 hours and 99.7% after 120 hours.

After filtration, devolatilization is carried out, after a temperature rise over two hours, at 120° C. under a vacuum of 1×10² Pa for 5 hours.

A colourless functionalized oil is recovered.

What is claimed is:

1. Process for the preparation of a nonturbid, functionalized silicone oil of stable viscosity, the process comprising: hydrosilylating polyorganohydrosiloxane with synthons wherein:
   (1) the synthons hydrosilylated with the polyorganohydrosiloxane are different or identical, comprising at least one hydrocarbon-comprising ring in which is included at least one oxygen atom,
   (2) said hydrosilylation reaction is carried out in the presence of a heterogeneous catalytic composition to reduce reactions that can form a gum and/or resin during devolatilization, the heterogeneous catalytic composition comprising a metal selected from the group consisting of cobalt, rhodium, ruthenium, platinum and nickel deposited on an inert support, said inert support selected from the group consisting of carbon black, charcoal, alumina, silicate and barium oxide, and
   (3) the polyorganohydrosiloxane is linear or cyclic and has the mean formulae;

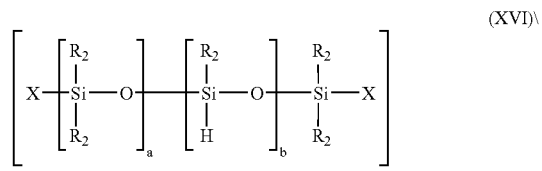

(XVI)

and/or

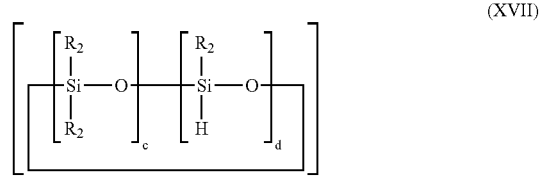

(XVII)

in which:
   the symbols R₂ are identical or different and correspond to a monovalent hydrocarbon-comprising radical chosen from the phenyl radical and linear or branched alkyl radicals having from 1 to 6 carbon atoms;
   the symbols x are identical or different and correspond to a monovalent radical chosen from R₂, a hydrogen atom, a methoxy radical and an ethoxy radical;
   a and b are integers or fractions, such that:
      $0 < a \leq 200$,
      $0 \leq b > 200$,
   and at least on of the two x groups corresponds to the hydrogen radical if b=0,
      $5 < a+b \leq 200$;

c and d are integers or fractions, such that:
0<c<5,
1<d<10,
3<c+d<10
wherein the synthon has the formula:

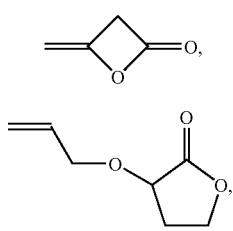
(X)

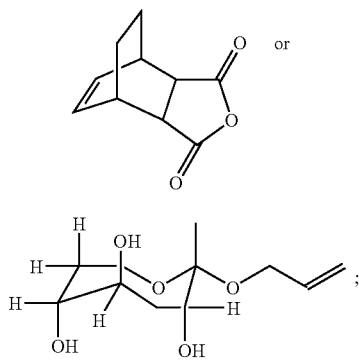
(XI)
(XII)
(XIII)
(XIV)
(XV)

and
(4) devolatilizing a silicone oil obtained from the hydrosilylation reaction wherein the functionalized oils obtained are colorless and prepared in the presence of said catalytic composition, the inert support for which is carbon black.

2. Process for the preparation of a nonturbid, functionalized silicone oil of stable viscosity, the process comprising: hydrosilylating polyorganohydrosiloxane with synthons wherein:
(1) the synthons hydrosilylated with the polyorganohydrosiloxane are different or identical, comprising at least one hydrocarbon-comprising ring in which is included at least one oxygen atom,
2) said hydrosilylation reaction is carried out in the presence of a heterogeneous catalytic composition to reduce reactions that can form a gum and/or resin during devolatilization, the heterogeneous catalytic composition comprising a metal selected from the group consisting of cobalt, rhodium, ruthenium, platinum and nickel deposited on an inert support, said inert support selected from the group consisting of carbon black, charcoal, alumina, silicate and barium oxide, and
(3) the polyorganohydrosiloxane is linear or cyclic and has the mean formulae:

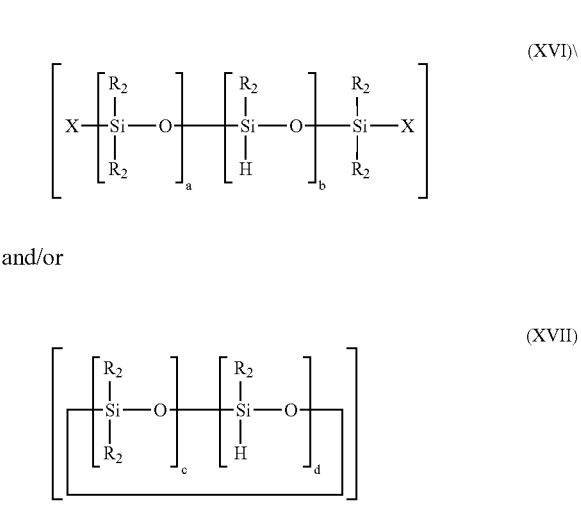
(XVI)

and/or (XVII)

in which:
the symbols $R_2$ are identical or different and correspond to a monovalent hydrocarbon-comprising radical chosen from the phenyl radical and linear or branched alkyl radicals having from 1 to 6 carbon atoms;
the symbols x are identical or different and correspond to a monovalent radical chosen from $R_2$, a hydrogen atom, a methoxy radical and an ethoxy radical;
a and b are integers or fractions, such that:
$0 < a \leq 200$,
$0 \leq b < 200$,
and at least one of the two x groups corresponds to the hydrogen radical if b=0,
$5 < a+b \leq 200$;
c and d are integers or fractions, such that:
0<c<5,
1<d<10,
3<c+d<10
wherein the synthon has the formula:

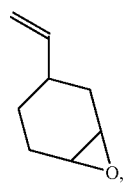
(IX)

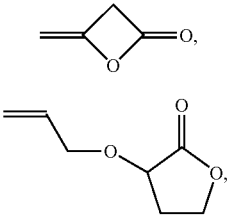
(X)

(XI)

-continued (XII)

(XIII)

(XIV)

(XV)

(4) devolatilizing a silicone oil obtained from the hydrosilylation reaction, wherein the polyorganohydrosiloxane and the synthon pass over or through a stationary bed of the catalytic composition.

3. Preparation process according to claim 2, wherein the functionalized oils obtained are colorless and prepared in the presence of said catalytic composition, the inert support for which is carbon black.

4. Process according to claim 2, wherein the polyorganohydrosiloxane/synthons molar ratio is between 0.01 and 100.

5. Process according to claim 2, wherein the amount of metal is between 0.1% and 5% with respect to the weight of the inert support.

6. Process according to claim 2, wherein the amount of metal in the catalytic composition is between 1 and 1000 ppm with respect to the weight of the polyorganohydrosiloxane.

7. Process according to claim 2, wherein the metal of the catalytic composition is platinum.

8. Process according to claim 2, comprising the following stages:
(a) introducing an amount of 5 to 5000 ppm of heterogeneous catalytic composition with respect to the total mass of the reactants under an inert gas into the reaction mixture;
(b) introducing the synthon into the reaction mixture;
(c) heating said mixture to a temperature of between 25° C. and 200° C.;
(d) subsequently introducing the polyorganohydrosiloxane over a period of time of between 0 and 24 hours, the synthon/polyorganohydrosiloxane molar ratio being between 1 and 1.10;
(e) filtering the reaction mass in order to separate the heterogeneous catalytic composition and the functionalized silicone oil; and
(f) finally devolatilizing the functionalized silicone oil.

9. Process for the preparation of a nonturbid, functionalized silicone oil of stable viscosity, the process comprising: hydrosilylating polyorganohydrosiloxane with synthons wherein:
(1) the synthons hydrosilylated with the polyorganohydrosiloxane are different or identical, comprising at least one hydrocarbon-comprising ring in which is included at least one oxygen atom,
(2) said hydrosilylation reaction is carried out in the presence of a heterogeneous catalytic composition to reduce reactions that can form a gum and/or resin during devolatilization, the heterogeneous catalytic composition comprising a metal selected from the group consisting of cobalt, rhodium, ruthenium, platinum and nickel deposited on an inert support, said inert support selected from the group consisting of carbon black, charcoal, alumina, silicate and barium oxide, and
(3) the polyorganohydrosiloxane is linear or cyclic and has the mean formulae:

$$\left[ X \begin{array}{c} R_2 \\ | \\ Si - O \\ | \\ R_2 \end{array} \right]_a \left[ \begin{array}{c} R_2 \\ | \\ Si - O \\ | \\ H \end{array} \right]_b \left[ \begin{array}{c} R_2 \\ | \\ Si - X \\ | \\ R_2 \end{array} \right] \quad (XVI)$$

and/or $$\left[ \begin{array}{c} R_2 \\ | \\ Si - O \\ | \\ R_2 \end{array} \right]_c \left[ \begin{array}{c} R_2 \\ | \\ Si - O \\ | \\ H \end{array} \right]_d \quad (XVII)$$

in which:
the symbols $R_2$ are identical or different and correspond to a monovalent hydrocarbon-comprising radical chosen from the phenyl radical and linear or branched alkyl radicals having from 1 to 6 carbon atoms;
the symbols x are identical or different and correspond to a monovalent radical chosen from $R_2$, a hydrogen atom, a methoxy radical and an ethoxy radical;
a and b are integers or fractions, such that:
$0 < a \leq 200$,
$0 \leq b < 200$,
and at least one of the two x groups corresponds to the hydrogen radical if b=0,
$5 < a+b \leq 200$;
c and d are integers or fractions, such that:
$0 < c < 5$,
$1 < d < 10$,
$3 < c+d < 10$ wherein the synthon has the formula:

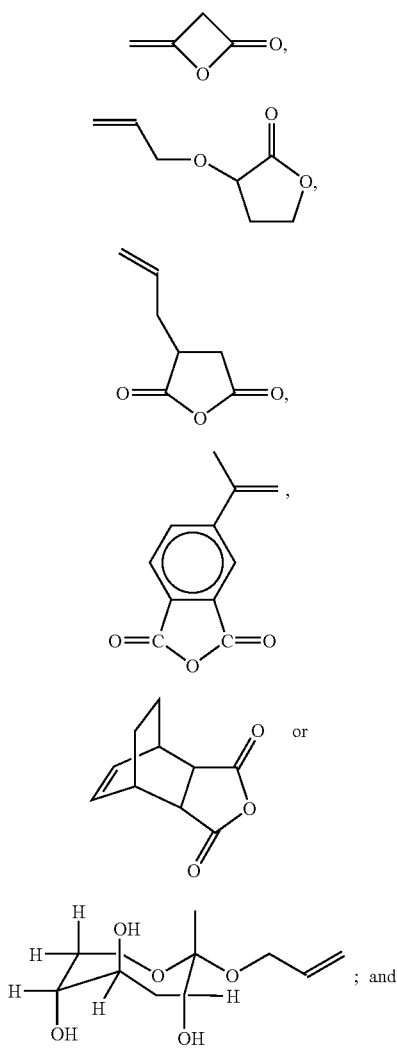

; and

10. Process according to claim 9, comprising the following stages:
    (a) introducing an amount of 5 to 5000 ppm of heterogeneous catalytic composition with respect to the total mass of the reactants under an inert gas into the reaction mixture;
    (b) introducing the synthon into the reaction mixture;
    (c) heating said mixture to a temperature of between 25° C. and 200° C.;
    (d) subsequently introducing the polyorganohydrosiloxane over a period of time of between 0 and 24 hours, the synthon/polyorganohydrosiloxane molar ratio being between 1 and 1.10;
    (e) filtering the reaction mass in order to separate the heterogeneous catalytic composition and the functionalized silicone oil; and
    (f) finally devolatilizing the functionalized silicone oil.

11. Process according to claim 9, wherein the polyorganohydrosiloxane and the synthon react in the reaction mixture in the absence of solvent.

12. The process according to claim 9, wherein the inert support of the heterogeneous catalytic composition is carbon black.

13. Process according to claim 9, wherein the polyorganohydrosiloxane/synthons molar ratio is between 0.01 and 100.

14. Process according to claim 9, wherein the amount of metal is between 0.1% and 5% with respect to the weight of the inert support.

15. Process according to claim 9, wherein the amount of metal in the catalytic composition is between 1 and 1000 ppm with respect to the weight of the polyorganohydrosiloxane.

16. Process according to claim 9, wherein the metal of the catalytic composition is platinum.

* * * * *